United States Patent
Best

Patent Number: 5,558,746
Date of Patent: Sep. 24, 1996

[54] APPARATUS FOR QUENCHING A GAS STREAM IN THE PRODUCTION OF VINYL CHLORIDE MONOMER

[75] Inventor: James E. Best, Paducah, Ky.

[73] Assignee: Westlake Monomers Corporation, Houston, Tex.

[21] Appl. No.: 475,566

[22] Filed: Jun. 7, 1995

Related U.S. Application Data

[62] Division of Ser. No. 355,918, Dec. 14, 1994, Pat. No. 5,507,921.

[51] Int. Cl.⁶ .............................. B01D 3/14; C10B 39/00; C07C 17/38
[52] U.S. Cl. .......................... 202/158; 202/227; 202/229; 203/99; 570/238
[58] Field of Search .................... 202/152, 154, 202/158, 161, 195, 227, 229; 203/98, 99, 94, DIG. 19; 570/238, 226, 220

[56] References Cited

U.S. PATENT DOCUMENTS

| | | | |
|---|---|---|---|
| 3,120,568 | 2/1964 | Brown | 260/654 |
| 3,468,967 | 9/1969 | Wall et al. | 260/656 |
| 3,655,787 | 4/1972 | Wiley | 260/656 R |
| 3,864,409 | 2/1975 | Pope | 570/238 |
| 3,867,263 | 2/1975 | Wall | 203/81 |
| 3,876,714 | 4/1975 | Riegel | 570/238 |
| 3,879,482 | 4/1975 | Coppens | 260/656 R |
| 3,920,761 | 11/1975 | Krome | 570/238 |
| 3,963,584 | 6/1976 | Tsao | 203/49 |
| 3,992,460 | 11/1976 | Tsao | 260/654 R |
| 4,094,915 | 6/1978 | Tsao | 260/656 R |
| 4,333,799 | 6/1982 | Crico | 203/67 |
| 4,642,400 | 2/1987 | Cowfer et al. | 570/238 |
| 4,760,206 | 7/1988 | Schneider | 570/220 |
| 4,788,357 | 11/1988 | Dummer et al. | 570/226 |
| 4,822,932 | 4/1989 | Dummer et al. | 570/226 |
| 5,122,235 | 6/1992 | Shirai et al. | 203/28 |
| 5,200,040 | 4/1993 | Naka et al. | 203/25 |

Primary Examiner—Christopher Kim
Attorney, Agent, or Firm—Ben D. Tobor

[57] ABSTRACT

A method and apparatus for quenching a gas stream in the production of vinyl chloride monomer includes the use of a knock back condenser and a plurality of column fractional distillation trays disposed within the quench column, and a liquid stream of 1,2-dichloroethane, vinyl chloride, and hydrogen chloride may be removed from the bottom column fractional distillation tray.

5 Claims, 3 Drawing Sheets

Fig. 3 *(PRIOR ART)*

APPARATUS FOR QUENCHING A GAS STREAM IN THE PRODUCTION OF VINYL CHLORIDE MONOMER

This is a division of application Ser. No. 08/355,918, filed Dec. 14, 1994 now U.S. Pat. No. 5,507,921.

BACKGROUND OF THE INVENTION

1. Field of the Invention

The invention relates to a method and apparatus for quenching a gas stream in the production of vinyl chloride monomer and, more particularly, a method and quench column for quenching a gas stream comprising vinyl chloride, hydrogen chloride, and unreacted 1,2-dichloroethane.

2. Description of the Prior Art

Few monomers are commercially produced in the world on so large a scale as vinyl chloride monomer ("VCM"). Over 95% of the VCM produced in the world is made by pyrolysis of 1,2-dichloroethane, or ethylene dichloride ("EDC"), in accordance with the following reaction:

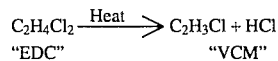
$$C_2H_4Cl_2 \xrightarrow{\text{Heat}} C_2H_3Cl + HCl$$
"EDC" "VCM"

This reaction typically takes place at elevated temperatures in the range of 900° F.–1000° F. within a cracking furnace having a plurality of pyrolysis furnace tubes. The EDC is thermally cracked to produce equal molar quantities of vinyl chloride and hydrogen chloride ("HCl"). Typically the cracking furnace is designed to convert 50% to 60% of the EDC feed per pass of the feed through the cracking furnace. Hot cracking furnace effluent gases containing vinyl chloride, hydrogen chloride, unreacted EDC, and undesired byproducts, including carbonaceous impurities, such as coke, and chlorinated organics, must be rapidly cooled in a quench column to stop the pyrolysis reactions and to minimize the formation of additional byproducts. Typically, in the prior art, these effluent gases are cooled by direct contact with cooled liquid EDC and vinyl chloride in the quench column.

A major portion of a VCM manufacturing plant's capital and operating costs are associated with the separation and purification of the cracking furnace effluent gas components. Fractional distillation processes are typically used to separate VCM and HCl products, and are used to remove undesired impurities from unreacted EDC for recycling to the cracking furnace feed stock.

There are many disadvantages associated with current quench column designs and methods of quenching utilized in the production of VCM. One disadvantage is the necessity to use relatively large capacity circulation pumps and piping, which result in substantial capital costs in constructing a VCM plant. There are process safety and environmental concerns resulting from circulated liquid containing undesired impurities, such as coke particles, which can cause severe pump maintenance problems and piping erosion. Historically, cracking furnace quench circulation piping failures have been a major source for VCM production plant fires. Another disadvantage associated with prior art quench column designs and methods of quenching is that it is difficult to remove coke particles, which causes relatively high fouling rates on VCM purification equipment and reduces equipment life. A further disadvantage associated with prior art quench column designs and methods of quenching is that poor component separation is achieved, which results in higher energy costs for the conventional downstream hydrogen chloride and vinyl chloride distillation process. An additional disadvantage of conventional methods and apparatus for quenching the cracking furnace effluent gas stream is that removal of solids from the quench column, such as coke particles, is typically done by filtering quench liquid which is removed from the bottom of the quench column. Filtering efficiency is typically very poor because conventional methods and apparatus tend to break up fragile coke particles into smaller particles which can pass through the filtering device.

Accordingly, prior to development of the present invention, there has been no method and apparatus for quenching a gas stream from an EDC cracking furnace which: does not require relatively large capacity circulation pumps and piping and their substantial capital costs; does not have process safety and environmental concerns arising from circulated liquid containing coke particles which can cause severe pump maintenance problems and piping erosion, and could lead to piping failures and resulting plant fires; easily permits the removal of coke particles from the quench column, whereby vinyl chloride purification equipment does not have relatively high fouling rates, which reduces equipment life; achieves good component separation, which results in lower energy usage for the downstream hydrogen chloride and vinyl chloride distillation process; and has substantial filtering efficiency to remove fragile coke particles. Therefore, the art has sought a method and apparatus for quenching a cracking furnace effluent gas stream which: does not require the use of relatively large capacity circulation pumps and piping, thereby having lower capital costs; does not have process safety and environmental concerns resulting from circulated liquid containing coke particles, thereby reducing pump maintenance problems and piping erosion; permits the easy removal of coke particles to avoid high fouling rates on vinyl chloride purification equipment, and increases equipment life; provides good component separation, which results in lower energy usage for the downstream hydrogen chloride and vinyl chloride distillation process; and achieves high filtering efficiency for the removal of coke particles.

SUMMARY OF THE INVENTION

In accordance with the invention, the foregoing advantages have been achieved through the present method of quenching a gas stream comprising vinyl chloride, hydrogen chloride, and unreacted 1,2-dichloroethane produced by the pyrolysis of 1,2-dichloroethane and containing undesired byproducts of pyrolysis. The present invention may include the steps of: providing a quench column, having an upper and lower end, the lower end of the quench column containing a quantity of quench liquid; introducing the gas stream directly into the quench liquid to cool the gas stream to cease the pyrolysis of the EDC and minimize the formation of additional byproducts, whereby EDC, vinyl chloride, and HCl vapors rise from the quench liquid; providing a plurality of column fractional distillation trays, with at least an upper column fractional distillation tray and a bottom fractional distillation tray, within the quench column above the quantity of quench liquid; passing the EDC, vinyl chloride, and HCl vapors upwardly through the plurality of column fractional distillation trays; introducing liquid EDC, vinyl chloride, and HCl into the upper end of the quench column, above the plurality of column fractional distillation trays; removing the EDC, vinyl chloride, and HCl vapors from the upper end of the quench column; and removing a liquid stream of EDC, vinyl chloride and HCl from the bottom column fractional distillation tray.

Another feature of the present invention is that the liquid EDC, vinyl chloride, and HCl may be introduced into the upper end of the quench column by providing a knock back condenser in the upper end of the quench column above the column fractional distillation trays, and partially condensing the rising EDC, vinyl chloride, and HCl vapors. An additional feature of the present invention is that the liquid EDC, vinyl chloride, and HCl may be introduced into the upper end of the quench column by providing a horizontally disposed condenser above the quench column; partially condensing the rising EDC, vinyl chloride, and HCl vapors; and introducing the liquid EDC, vinyl chloride, and HCl from the horizontally disposed condenser into the upper end of the quench column. The liquid EDC, vinyl chloride, and HCl may be flowed into the upper end of the quench column by only utilizing the force of gravity, whereby no pump is utilized to introduce the liquid EDC, vinyl chloride, and HCl. A further feature of the present invention may include the step of removing from the bottom of the quench column a portion of the quench liquid containing the undesired byproducts of pyrolysis, and filtering out the undesired byproducts of pyrolysis.

In accordance with another aspect of the present invention, the foregoing advantages have been achieved by the present quench column for quenching a gas stream comprising vinyl chloride, HCl, and unreacted EDC produced by the pyrolysis of EDC and containing undesired byproducts of pyrolysis. This aspect of the present invention may include: a vertically disposed vessel having an upper and a lower end, the lower end adapted to contain a quantity of quench liquid; at least one nozzle disposed in the lower end of the vessel and adapted to be disposed within the quantity of quench liquid; a plurality of column fractional distillation trays, with at least an upper column fractional distillation tray and a bottom column fractional distillation tray, disposed within the vessel, above the at least one nozzle; and a means for introducing liquid EDC, vinyl chloride, and HCl into the upper end of the vessel above the plurality of column fractional distillation trays.

Another feature of this aspect of the present invention is that the means for introducing may be a knock back condenser disposed in the upper end of the vessel above the column fractional distillation trays. A further feature of this aspect of the present invention is that the means for introducing may be a horizontally disposed condenser disposed above the vessel, and the liquid EDC, vinyl chloride and HCl flow from the horizontally disposed condenser into the upper end of the vessel only under the force of gravity. An outlet means may be disposed at the lower end of the vessel for draining a portion of the quench liquid from the vessel, and the outlet means may be in fluid communication with a means for filtering a quench liquid to remove undesired byproducts of pyrolysis.

The method and apparatus for quenching a gas stream from the pyrolysis of EDC, when compared with previously proposed prior art methods and apparatus, has the advantages of: improving separation of the cracking furnace effluent components of EDC, vinyl chloride, HCl, byproducts and coke particles, which improves downstream HCl distillation efficiency and reduces coke particle removal costs; permits cooling of the gas stream without the use of circulation pumps and associated piping, thereby eliminating pump maintenance costs and environmental hazards associated with pump and/or piping leaks; and increases filtering efficiency of undesired coke particles.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
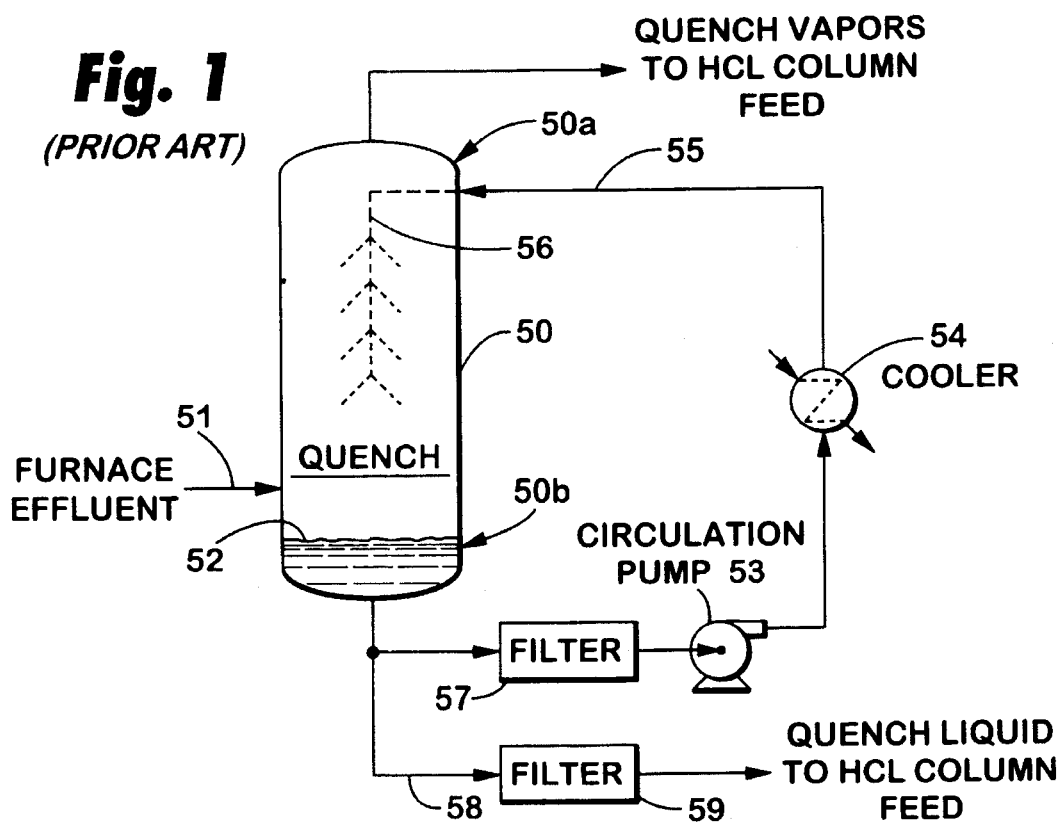
FIG. 1 is a process flow sheet of a conventional quench column section in a commercial plant for the production of VCM from EDC.

With reference to FIG. 1, a prior art quench column 50 and method for quenching a gas stream from a conventional cracking furnace (not shown) will be described. Furnace effluent gases 51, which contain vinyl chloride, HCl, unreacted EDC, and byproducts, such as coke particles and chlorinated organics, pass from the cracking furnace into the lower end of quench column 50. The furnace effluent gases 51 are cooled by direct contact with cooled, liquid EDC and vinyl chloride in the quench column 50. For the purpose of clarity, the term "vinyl chloride" ("VCl") is used herein when the vinyl chloride is in-process, that is, first formed and subsequently processed in the VCl purification section of a VCM plant (not shown). The term "vinyl chloride monomer" ("VCM") is used when the VCl has been purified, that is finished, so that it meets product VCM specifications. The cooled, liquid EDC and VCl is obtained in the following manner. Quench liquid 52 from the lower end 50b of quench column 50 is pumped by circulation pump 53 through a cooler, or heat exchanger, 54 and returned to the upper end 50a of the quench column 50 through conventional piping 55 and a liquid feed distribution system 56 disposed in the upper end 50a of quench column 50. The furnace effluent gases 51 are cooled by direct contact with the circulated liquid in the quench column 50. A filter 57 is disposed within piping 55 between the lower end 50b of quench column 50 and circulation pump 53, to filter out undesired byproducts of pyrolysis, such as fine coke particles (not shown). During operation of quench column 50, quench vapors including unreacted EDC, VCl, and HCl, pass upwardly through quench column 50, and are removed from the upper end 50a of quench column 50, and are conveyed in a conventional manner to the upper end of a conventional HCl distillation column (not shown). Quench liquid, including a liquid stream of unreacted EDC, VCl, and HCl, are removed from the lower end 50b of quench column 50 through conventional piping 58. The quench liquid is conveyed in a conventional manner to the bottom of a conventional HCl distillation column (not shown). A conventional filter 59 is provided in piping 58 to remove undesired solids from the quench liquid.

As previously discussed, there are many disadvantages associated with the quench column 50 and method of quenching illustrated in FIG. 1. Relatively large capacity circulation pumps 53 and piping 55 are required with the quench column 50 of FIG. 1, which increases the capital costs associated with utilizing such a quench column 50 and method for quenching the furnace effluent gases. The circulated, cooled liquid which passes through piping 55 normally contains fine coke particles which can cause severe pump maintenance problems and erosion of piping 55. When utilizing the quench column 50 and method for quenching of FIG. 1, it is difficult to remove the fine coke particles, which in turn causes relatively high fouling rates on VCl purification equipment (not shown). It has also been found that poor separation of the furnace effluent gas components is achieved, which results in higher energy usage for the downstream HCl/VCl distillation process. Additionally, the filtering efficiency of filters 57 and 59 is typically very poor because the relatively high flow velocities of circulation pump 53 tends to break up the fragile coke particles into smaller particles which can readily pass through the filter elements of filters 57, 59.

Figure 2:
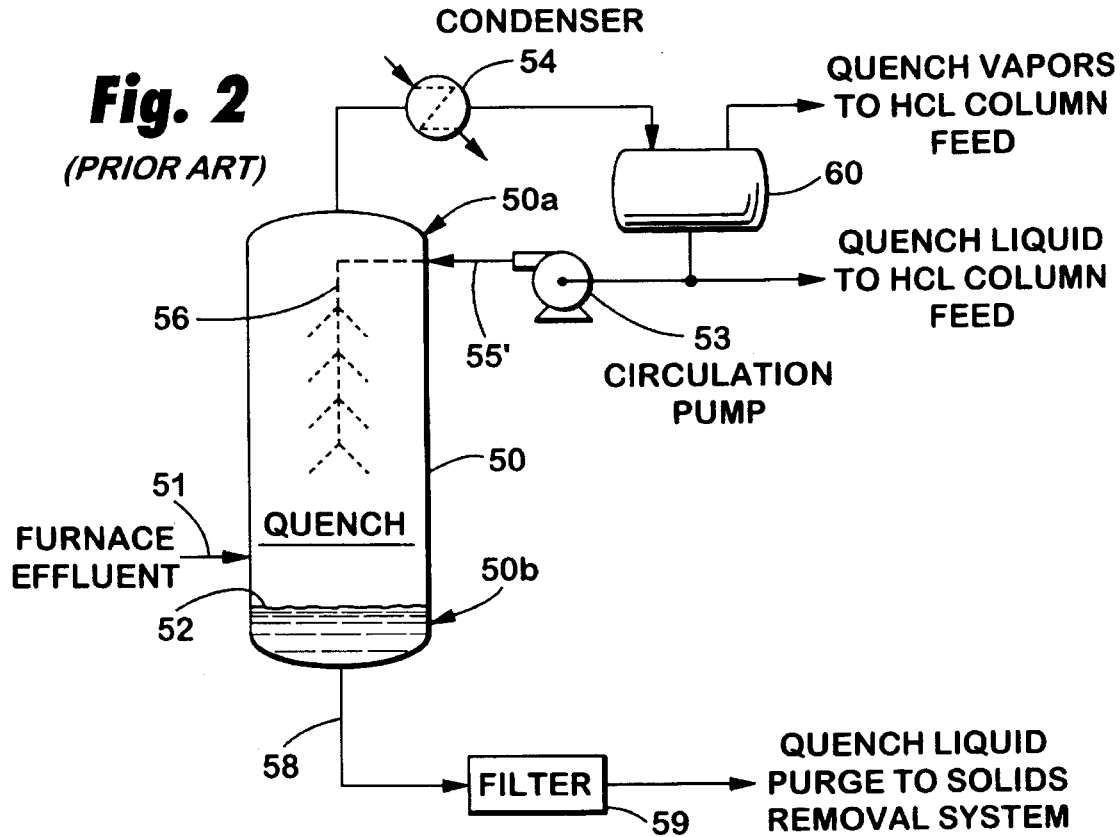
FIG. 2 is a process flow sheet of another type of conventional quench column section in a commercial plant for the production of VCM from EDC.

With reference to FIG. 2, another prior art quench column and method for quenching will be described. Hereinafter, identical reference numerals will be used for identical components previously described, and primed reference numerals will be utilized for components similar to those components previously described. In the quench column 50 of FIG. 2, a circulated, cool liquid is also introduced into the upper end 50a of quench column 50 via liquid feed distribution system 56, through the use of piping 55' and circulation pump 53, whereby the furnace effluent gases 51 are cooled by direct contact with the cooled liquid EDC and VCl in the manner previously described in connection with FIG. 1. In the method of quenching of FIG. 2, the cooled liquid EDC and VCl is obtained by condensing quench overhead vapors of VCl, HCl, and unreacted EDC which pass from the upper end 50a of quench column 50 through a condenser, or heat exchanger 54, and the circulated, cooled, condensed liquid is pumped by circulation pump 53 through piping 55' and into the liquid feed distribution system 56 in the upper end 50a of quench column 50. A conventional separator tank 60 is disposed within piping 55', which permits quench vapors and quench liquid to be withdrawn and fed to the HCl distillation column as previously described in connection with FIG. 1. Solids are removed from the lower end 50b of quench column 50 and pass through piping 58 and filter 59 as previously described in connection with FIG. 1. The quench liquid from piping 58 is then conveyed to a solids removal system (not shown) which may include treatment of the quench bottoms liquid in a series of flash tanks (not shown) or treatment in a small stripper column (not shown) to remove HCl and VCl. EDC in the quench bottoms purge stream from piping 58 is separated from solids in an EDC tars still (not shown) or in an EDC vacuum distillation column. Removal of HCl and VCl from the quench EDC purge stream is essential for smooth operation of these EDC distillation columns.

Although the quench column 50 and method of quenching of FIG. 2 offers some improvements over the quench column 50 and method of quenching of FIG. 1, in that the circulated liquid is relatively clean, since it contains little or no coke particles, there are still several disadvantages associated with the prior art quench column 50 and method for quenching of FIG. 2. Large capacity circulation pumps 53 and piping 55' are still required, relatively poor component separation is obtained, and there is still some degree of quench column pump and/or piping hazards and associated maintenance costs.

Figure 3:
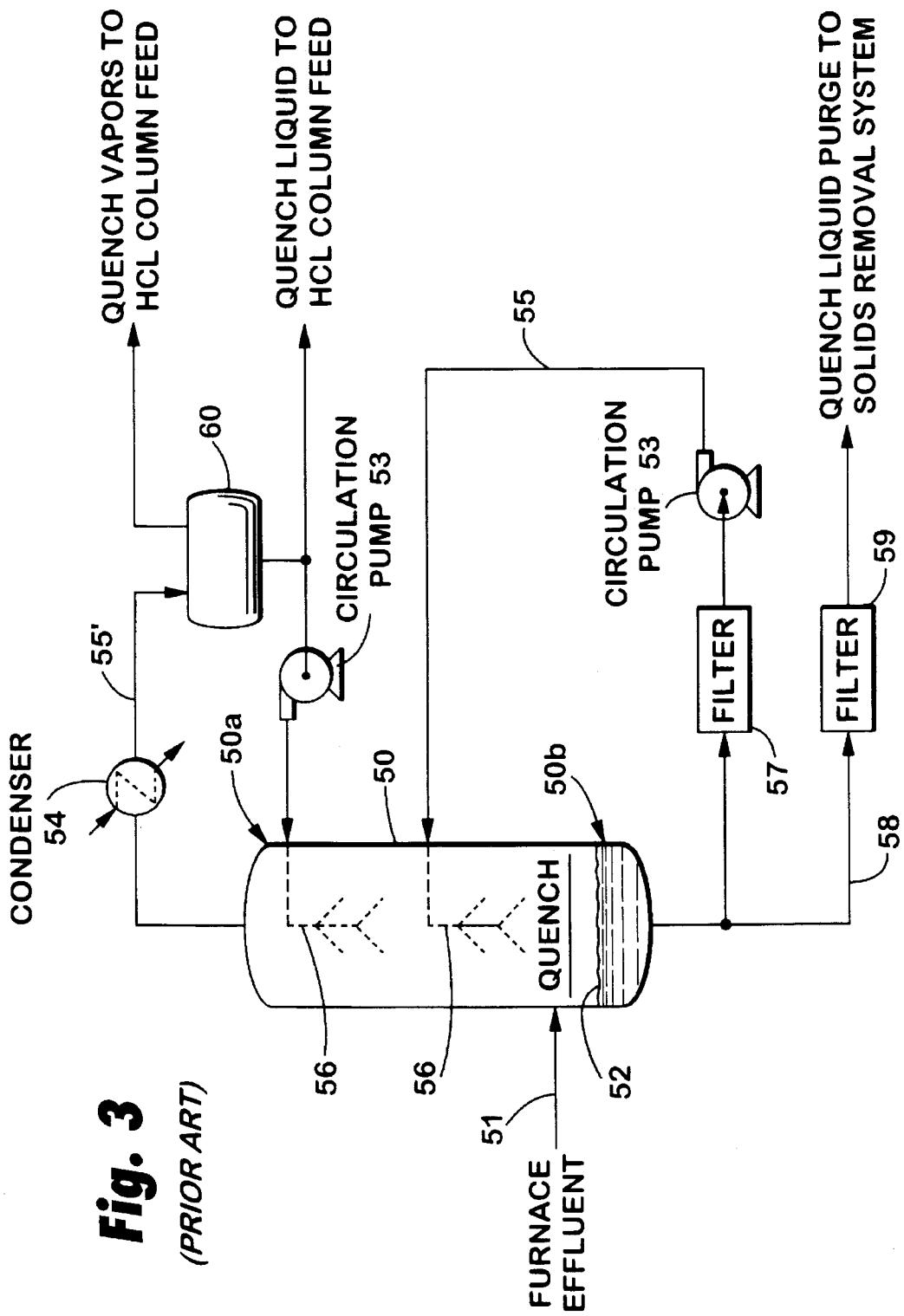
FIG. 3 is a process flow sheet of another conventional quench column section in a commercial plant for the production of VCM from EDC.

With reference to FIG. 3, another prior art quench column 50 and method for quenching furnace effluent gases 51 will be described. Quench column 50 of FIG. 3 incorporates circulation of two cooled liquid streams, which include cooled liquid EDC and VCl. The quench column 50 of FIG. 3 combines the components of the FIG. 1 embodiment with the components of the FIG. 2 embodiment, all as previously described in connection with FIGS. 1 and 2, with the exception that cooler, or heat exchanger, 54 of FIG. 1 is not used in connection with piping 55. Accordingly, the quench column 50 of FIG. 3 incorporates circulation of an overhead condensed liquid stream from piping 55' and a liquid bottoms stream from piping 55, both of which pass into quench column 50 through liquid feed distribution systems 56. The quench column 50 and method for quenching furnace effluent gases of FIG. 3 has all of the disadvantages previously described in connection with the quench columns 50 and methods for quenching, of FIGS. 1 and 2, with the further disadvantages of even higher capital costs for the necessary circulation pumps 53 and piping 55, 55'. Additionally, because of the increased piping 55, 55' and the use of multiple circulation pumps 53, there are even higher risks for piping leaks and potential plant fires resulting from such leaks.

Figure 4:
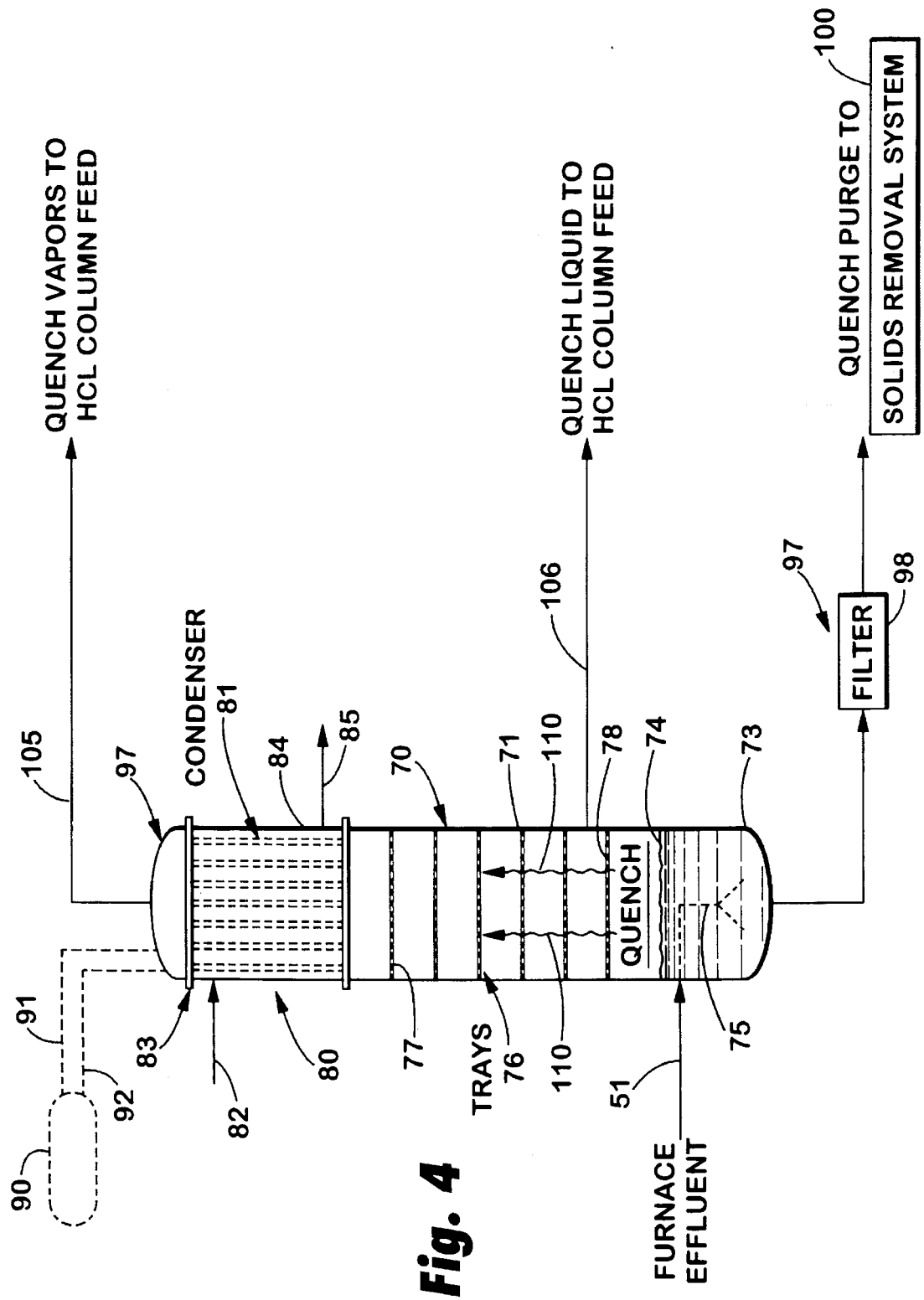
FIG. 4 is a process flow sheet of a quench column section, in accordance with the present invention, in a commercial plant for the production of VCM from EDC.

With reference to FIG. 4, the quench column 70 and method of quenching a gas stream, in accordance with the present invention, will be described. Quench column 70 generally includes: a vertically disposed pressure vessel 71 having an upper end 72 and a lower end 73, the lower end 73 adapted to contain a quantity of quench liquid 74; at least one nozzle 75 disposed in the lower end 73 of the vessel 71, and the at least one nozzle 75 is disposed and submerged within the quantity of quench liquid 74; a plurality of column fractional distillation trays 76, with at least an upper column fractional distillation tray 77 and a bottom column fractional distillation tray 78, disposed within the vessel 71, above the at least one nozzle 75 and a means for introducing 80 liquid EDC, VCl, and HCl into the upper end 72 of the vessel 71 above the plurality of column fractional distillation trays 76. Preferably, eight column fractional distillation trays 76, of conventional design, are provided in vessel 71.

Still with reference to FIG. 4, the means for introducing 80 liquid EDC, VCl, and HCl is preferably a knock back condenser 81 disposed in the upper end 72 of the vessel 71, and the knock back condenser 81 is disposed above the plurality of column fractional distillation trays 76. A suitable cooling medium 82 enters the upper end 83 of knock back condenser 81 and flows through the condenser and exits the lower end 84 of knock back condenser 81 at exit pipe 85. Alternatively, as shown in phantom lines in FIG. 4, the means for introducing 80 liquid EDC, VCl, and HCl may be a horizontally disposed condenser 90, of conventional design, disposed above vessel 71. A quench vapor inlet pipe 91 permits quench vapors from vessel 71 to pass upwardly into condenser 90, and upon the quench vapors being condensed within condenser 90, liquid EDC, VCl, and HCl flow from the condenser 90 back into the upper end 72 of vessel 71. Because condenser 90 is disposed above vessel 71, the liquid EDC, VCl, and HCl will flow from condenser 90 through pipe, or flow passageway 92 into the upper end 72 of vessel 71 only under the force of gravity, with no circulation pump being necessary or utilized.

Still with reference to FIG. 4, an outlet means 95, such as pipe, or flow passageway, 96 is disposed at the lower end 73 of vessel 71, and may be utilized for draining a portion of the quench liquid 74 from vessel 71. The outlet means 95 is in fluid communication with a means for filtering 97, or filter 98, of conventional design, for filtering the quench liquid 74 to remove undesired byproducts of pyrolysis, including particles of coke. The filtered quench liquid exiting from filtering means 97 may then pass through conventional piping 99 and may be conveyed directly to a solids removal system 100, or conveyed directly to a series of flash tanks (not shown) or a small stripper column (not shown) to remove HCl and VCl.

The upper end 72 of vessel 71 includes a fluid passageway, or pipe, 105 for conveying quench vapors from the vessel 71 to a conventional HCl distillation column (not shown). A suitable, conventional pipe 106 is in fluid communication with the bottom column fractional distillation tray 78, and permits the removal of a liquid stream of EDC, VCl, and HCl from the bottom column fractional distillation tray 78, which is conveyed to a conventional HCl distillation column (not shown).

Still with reference to FIG. 4, the method of quenching a gas stream comprising VCl, HCl, and unreacted EDC, produced by the pyrolysis of EDC and containing undesired byproducts of pyrolysis, in accordance with the present invention, will be described. The hot, furnace effluent gases 51 enter the lower end 73 of vessel 71 and pass through nozzle 75, which is submerged within the quantity of quench liquid 74. The at least one nozzle 75 provides natural liquid circulation of the quench liquid 74 within the lower end 73 of vessel 71, and further provides immediate contact of the furnace effluent gases 51 with the quench liquid 74, whereby the furnace effluent gases, or gas stream comprising VCl, HCl, and unreacted EDC are immediately cooled. Accordingly, cooling of the furnace effluent gas stream ceases the pyrolysis of the EDC and minimizes the formation of additional byproducts, while EDC, VCl, and HCl vapors, or quench vapors, 110 rise from the quantity of quench liquid 73 upwardly through vessel 71. As the rising quench vapors 110 pass upwardly through vessel 71, the vapors 110 are partially condensed when they contact the coils of knock back condenser 81, whereby liquid EDC, VCl, and HCl are thereby introduced into the upper end 72 of vessel 71. Liquid EDC, VCl, and HCl then flow downwardly within vessel 71, without the use of any pumps or piping, and this liquid passes downwardly through the plurality of column fractional distillation trays 76, which serve to separate the EDC, VCl, and HCl components. A liquid stream of EDC, VCl, and HCl may be removed by piping 106 from the bottom column fractional distillation tray 78, which liquid stream, or quench liquid, is then conveyed to the HCl distillation column (not shown) as previously described. The upwardly rising EDC, VCl, and HCl vapors, or quench vapors 110, which are not condensed by contacting knock back condenser 81, pass upwardly through piping 105 and are conveyed to the HCl distillation column (not shown) as previously described.

Alternatively, condenser 90 may be utilized in lieu of knock back condenser 81, as the means for introducing liquid EDC, VCl, and HCl into the upper end 72 of vessel 71. Once again, the utilization of condenser 90 provides quench liquid 74, as well as the quench liquids which are drained from the bottom column fractional distillation tray 78, as previously described.

It has been discovered by utilizing the plurality of column fractional distillation tray 76 within vessel 71, and withdrawing quench vapors 110 from the upper end 72 of vessel 71 and withdrawing quench liquid from the bottom column fractional distillation tray 78, as previously described, four to six theoretical separation stages may be achieved, rather than only one to two theoretical separation stages achieved with a conventional quench column of equivalent height. By increasing the number of theoretical separation stages within vessel 71, there is a significant improvement in component separation. It has been found that the quench vapors 110 removed from the upper end 72 of vessel 71 contain less EDC and more VCl and HCl, while the quench liquid removed from the bottom column fractional distillation tray 78 contains less VCl and HCl, and more EDC. Both of these results permit improved performance in the HCl distillation column, as well as improved performance of the solid removal system 100. Table 1, set forth below, illustrates the improved component separation obtained through use of the quench column 70 and method for quenching a gas stream, of the present invention, when compared with the prior art quench columns and methods of quenching of FIGS. 1–3.

| Quench Product Streams | FIG. 1 Design | FIGS. 2 & 3 Design | FIG. 4 Design |
|---|---|---|---|
| Quench Vapors Feed to HCl Column: | | | |
| Weight % EDC | 3.46 | 1.96 | Trace |
| Weight % VCl | 40.51 | 30.24 | 40.43 |
| Weight % HCl | 56.02 | 67.80 | 59.57 |
| Quench Liquid Feed to HCl Column: | | | |
| Weight % EDC | 61.37 | 53.96 | 61.45 |
| Weight % VCl | 36.07 | 37.42 | 37.01 |
| Weight % HCl | 2.56 | 8.61 | 1.54 |

The foregoing data was obtained from a process computer simulation, and preliminary lab and plant data conform to the computer simulation data. The same operating parameters for each design were utilized.

The use of the quench column 70 and method of quenching a gas stream, in accordance with the present invention also provides increased filtering efficiency by filter 98 because of reduced quench liquid 74 flow velocity in vessel 71 and through pipe 96 to filter 98. The coke particles in the furnace effluent gases 51 are quite fragile, and typically break up into smaller particles which may pass through the filter elements (not shown) of filter 98 when used in connection with prior art quench column designs as illustrated in FIGS. 1–3, which operate at higher liquid flow velocities than that of quench column 70 in accordance with the present invention. Accordingly, filtering efficiency is greatly improved in the quench column 70 and method for quenching a gas stream, in accordance with the present invention. It has been found that the quench liquid 74 after passing through filter 98 may be conveyed directly to HCl and VCl distillation equipment, or alternatively, may be fed to a solid removal system 100. The improved component separation obtained by quench column 70, and the method of quenching a gas stream, in accordance with the present invention, simplifies the design of the solid removal system 100.

Another advantage obtained through use of the quench column 70, and method of quenching a gas stream, in accordance with the present invention, is that unreacted EDC may be recycled directly back into the feed for the cracking furnace, until the cracking furnace effluent gas temperature increases sufficiently to produce enough HCl and VCl to pressure up the quench column 70, and the volume of unreacted EDC in the quench vapors is reduced enough to minimize HCl and VCl distillation boil up problems. Improved quench component separation obtained from the use of quench column 70, in accordance with the present invention, makes this recycle start-up technique feasible. In prior art cracking furnace start-ups, there are typically plant operating problems due to the excessive quantities of unreacted EDC and low quench operating pressure resulting from the use of prior art quench columns such as shown in FIGS. 1–3.

It is to be understood that the invention is not to be limited to the exact details of construction, operation, exact materials, or embodiments shown and described as obvious modifications and equivalents will be apparent to one skilled in the art, for example, a conventional condenser design and pumps could be used to introduce liquid EDC, VCl, and HCl into the upper end of the quench column, above the plurality of column fractional distillation trays. Accordingly, the invention is therefore to be limited only by the scope of the appended claims.

I claim:

1. A quench column for quenching a gas stream including vinyl chloride, hydrogen chloride, and unreacted 1,2-dichloroethane produced by the pyrolysis of 1,2-dichloroethane and containing undesired byproducts of pyrolysis, comprising:

(a) a vertically disposed vessel having an upper and a lower end, the lower end adapted to contain a quantity of quench liquid;

(b) at least one nozzle disposed in the lower end of the vessel and adapted to be disposed within the quantity of quench liquid;

(c) a plurality of column fractional distillation trays, with at least an upper column fractional distillation tray and a bottom column fractional distillation tray, disposed within the vessel, above the at least one nozzle; and (d) a means for introducing liquid unreacted 1,2-dichloroethane, vinyl chloride, and hydrogen chloride into the upper end of the vessel above the plurality of column fractional distillation trays.

2. The quench column of claim 1, wherein the means for introducing is a knock back condenser disposed in the upper end of the vessel above the column fractional distillation trays.

3. The quench column of claim 1, wherein the means for introducing is a horizontally disposed condenser disposed above the vessel and the liquid, 1,2-dichloroethane, vinyl chloride, and hydrogen chloride flow from the horizontally disposed condenser into the upper end of the vessel only under the force of gravity.

4. The quench column of claim 1, wherein an outlet means is disposed at the lower end of the vessel for draining a portion of the quench liquid from the vessel.

5. The quench column of claim 4, wherein the outlet means is in fluid communication with a means for filtering the quench liquid to remove undesired byproducts of pyrolysis.

* * * * *